United States Patent [19]

Williams

[11] 4,143,073

[45] Mar. 6, 1979

[54] PROCESS FOR PREPARING SUBSTITUTED N-ALKOXY-N-SUBSTITUTED-2,6-DINITROANILINES

[75] Inventor: James C. Williams, Indianapolis, Ind.

[73] Assignee: Eli Lilly and Company, Indianapolis, Ind.

[21] Appl. No.: 810,228

[22] Filed: Jun. 27, 1977

[51] Int. Cl.$^2$ .............................................. C07C 85/04
[52] U.S. Cl. ........................................ 260/574; 71/121
[58] Field of Search ..................... 260/574, 577, 576; 71/121

[56] References Cited

U.S. PATENT DOCUMENTS

| | | | |
|---|---|---|---|
| 2,809,994 | 10/1957 | Hinckley | 260/574 |
| 3,121,745 | 2/1964 | Pawloski | 260/577 |
| 3,484,487 | 12/1969 | Dix | 260/577 |
| 3,920,739 | 11/1975 | Suda et al. | 260/577 X |

OTHER PUBLICATIONS

Morrison et al., "Organic Chemistry", 2nd Ed., p. 492 (1966).

Primary Examiner—Winston A. Douglas
Assistant Examiner—John Doll
Attorney, Agent, or Firm—Dwight E. Morrison; Arthur R. Whale

[57] ABSTRACT

A process is described for reacting substituted N-alkoxy-2,6-dinitroanilines with a $C_1$–$C_3$ alkyl halide, or a $C_3$–$C_4$ alkenyl halide, in the presence of sodium hydride, to yield substituted N-alkoxy-N-substituted-2,6-dinitroanilines, which are active as herbicides.

5 Claims, No Drawings

PROCESS FOR PREPARING SUBSTITUTED N-ALKOXY-N-SUBSTITUTED-2,6-DINITROANILINES

BACKGROUND OF THE INVENTION

1. Field of the Invention

This invention relates to a new process for the preparation of novel substituted N-alkoxy-N-substituted-2,6-dinitroanilines.

2. Description of the Prior Art

Various 2,6-dinitroanilines have been described in the chemical literature. Hantzsch, *Deutsche Chemische Gesellschaft Berichte*, 43, 1662–1685 (1910) discloses N,N-dipropyl-4-methyl-2,6-dinitroaniline and N,N-dimethyl-4-methyl-2,6-dinitroaniline. Joshi et al., *C. A.* 28, 469 (1934) disclose N,N-dimethyl-4-iodo-2,6-dinitroaniline, N,N-dimethyl-4-bromo-2,6-dinitroaniline, 4-iodo-2,6-dinitrophenylpiperidine, and 4-bromo-2,6-dinitrophenylpiperidine. Borsche et al., *C. A.* 5, 2079 (1911) disclose 2,6-dinitrophenylpiperidine. Daudt et al. U.S. Pat. No. 2,212,825, disclose a number of 2,6-dinitroanilines bearing a trifluoromethyl group in the 4-position. The preparative methods described in the above references are completely different from the novel method disclosed and claimed in the instant application.

The utility of 2,6-dinitroanilines in agriculture was first disclosed in Soper, U.S. Pat. Nos. 3,111,403; 3,257,190; 3,332,769; and 3,367,949. Soper disclosed such compounds to possess herbicidal activity, notably preemergent herbicidal activity. Following Soper, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924 and Belgian Pat. No. 787,939. The methods of preparing the 2,6-dinitroanilines disclosed in the references as cited in this paragraph are also different from the novel process disclosed and claimed in the instant aplication.

SUMMARY OF THE INVENTION

This invention relates to a novel method for preparing substituted N-alkoxy-N-substituted-2,6-dinitroanilines, active as herbicides.

DESCRIPTION OF THE PREFERRED EMBODIMENT

This invention relates to a novel method of preparing compounds of the formula:

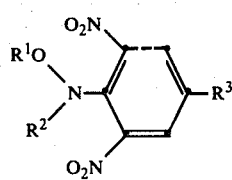

(I)

wherein
$R^1$ is methyl or ethyl;
$R^2$ is $C_1$–$C_3$ alkyl or $C_3$–$C_4$ alkenyl; and
$R^3$ is methyl, ethyl, or trifluoromethyl, which comprises allowing a compound of the formula:

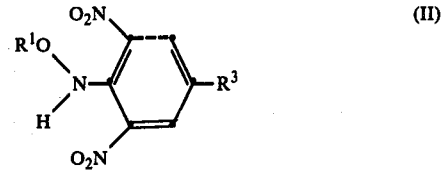

(II)

to react with a $C_1$–$C_3$ alkyl halide or a $C_3$–$C_4$ alkenyl halide, in the presence of sodium hydride.

In the above generic formulae, $C_1$–$C_3$ alkyl is represented by methyl, ethyl, n-propyl, and isopropyl; while $C_3$–$C_4$ alkenyl is represented by allyl, crotyl, and methallyl.

The novel compounds prepared by this novel method are disclosed and claimed in copending application Ser. No. 810,229, filed of even date, now U.S. Pat. No. 4,087,460. The novel compounds possess activity as herbicides.

The substituted N-alkoxy-2,6-dinitroanilines used as starting materials in the novel process of this invention are also disclosed and claimed in copending application Ser. No. 810,229, filed of even date, referred to supra. The preparation of these N-alkoxy intermediate compounds is illustrated as follows. 2,6-Dinitro-4-methylchlorobenzene in methanol is allowed to react with ethoxyamine hydrochloride in the presence of triethylamine for a sufficient time to bring about substantially complete reaction. This reaction is initiated at room temperature and the progress of the reaction is followed by thin layer chromatography (TLC) or by nuclear magnetic resonance spectroscopy (NMR) at about 30 minute intervals after the start of the reaction. Reaction times vary, and apparently are influenced by the identity of the 4-substituent of the 2,6-dinitrobenzene compounds used in the reaction, the 4-trifluoromethyl-2,6dinitrohalobenzene compounds being the most reactive. The reaction times therefore vary from about an hour or so at room temperature to as much as about 18 hours at reflux temperature in the case where the reactants are less reactive. When the reaction appears to be substantially completed, the reaction mixture is worked up to yield the desired product, which, in the instant example, is identified as 2,6-dinitro-N-ethoxy-p-toluidine, having a melting point of about 64°–66° C. The novel N-alkoxy compounds obtained by this process are useful as intermediates useful in the novel method of preparation of the novel compounds coming within the scope of generic formula (I), supra, which compounds possess herbicidal activity. Some of these novel intermediate compounds are also herbicidal in their activity.

The novel process of this invention is carried out by allowing a substituted N-alkoxy-2,6-dinitroaniline to react with a suitable alkylating agent in the presence of sodium hydride as the base, using dimethylformamide as the solvent of choice, at a temperature and for a time sufficient to bring about substantial completion of the reaction. Suitable alkylating agents for use in the novel method include methyl iodide, methyl bromide, methyl chloride, ethyl iodide, ethyl bromide, ethyl chloride, n-propyl bromide, n-propyl chloride, n-propyl bromide, n-propyl chloride, n-propyl iodide, isopropyl bromide, isopropyl chloride, isopropyl iodide; $C_1$–$C_3$ alkyl sulfates such as methyl sulfaate, ethyl sulfate, n-propyl sulfate, isopropyl surface; $C_3$–$C_4$ alkenyl halides such as allyl bromide, allyl chloride, crotyl chloride, crotyl bromide, methallyl chloride and methallyl bromide.

Suitable reaction temperatures range from ambient room temperature to about 110° C. The time of reaction may be as brief as 30 minutes at room temperature for the most reactive N-alkoxy-2,6-dinitroanilines and as long as several hours at about 90°-110° C. for the less reactive N-alkoxy-2,6-dinitroanilines.

The solvent of choice is dimethylformamide and the base of choice is sodium hydride. The novel method of preparation is illustrated as follows. A mixture of 2,6-dinitro-N-ethoxy-p-toluidine and sodium hydride in dimethylformamide is allowed to stir at room temperature for a short period of time, suitably about 10 minutes. At the end of that time the alkylating agent, for example, allyl bromide, is added to the reaction mixture, and the mixture is stirred for such period of time as to bring about substantially complete reaction, which in the instant example is about one hour. The progress of the reaction may be followed at about 30 minute intervals by thin-layer chromatography (TLC).

The reaction product mixture may be worked up by adding water and dilute aqueous acid, suitably dilute aqueous hydrochloric acid. In some cases the product precipitates or crystallizes out of the acidified mixture, and is filtered off. In other cases, a water-immiscible solvent, such as ether, ethyl acetate, or toluene, is added to extract the product from the aqueous acidified mixture. The organic solution is separated and dried over a suitable drying agent, for example anhydrous magnesium sulfate. The drying agent is then filtered off and the filtrate concentrated in vacuo to remove the solvent and leave a residue. This residue is then dissolved in a suitable solvent, for example toluene, and chromatographed over a Florisil column using toluene as the eluent. The eluate from the column is concentrated and the residue thus obtained is identified by NMR spectrum and elemental analyses; in the instant example the product is identified as N-allyl-2,6-dinitro-N-ethoxy-p-toluidine.

The preparations of the substituted N-alkoxy-2,6-dinitroanilines necessary for carrying out the novel process of this invention are illustrated by the preparations which follow.

PREPARATION 1

2,6-Dinitro-N-ethoxy-p-toluidine

A suspension of 10.0 g. (0.046 mole) of 2,6-dinitro-4-methylchlorobenzene in 100 ml. of methanol was prepared, and to the suspension there was added 7.6 g. (0.092 mole) of ethoxyamine hydrochloride, and 13.9 g. (0.138 mole) of triethylamine. The reaction mixture was stirred for about 30 minutes at room temperature and then heated and stirred for about 2-3 hours, checking samples from the mixture by NMR at half-hour intervals to follow the progress of the reaction. At this time an additional 16.7 g. (0.20 mole) of ethoxyamine hydrochloride was added, and the reaction mixture was stirred and refluxed for about 24 hours. An NMR spectrum of the reaction mixture indicated the presence of the desired product in about 70 percent yield. The reaction product mixture was poured over a mixture of ice and water, and the aqueous mixture filtered. The solid obtained was recrystallized from petroleum ether (b.p. 60°-71° C.) to yield 5.5 g. of product having a melting point of about 64°-66° C. The product was identified by its NMR spectrum as 2,6-dinitro-N-ethoxy-p-toluidine.

PREPARATION 2

2,6-Dinitro-4-ethyl-N-methoxyaniline

A suspension of 10.0 g. (0.043 mole) of 2,6-dinitro-4-ethylchlorobenzene in 100 ml. of methanol was prepared, and to the suspension there was added 14.7 g. (0.176 mole) of methoxyamine hydrochloride, and 22.2 g. (0.22 mole) of triethylamine, and the mixture was refluxed overnight. An additional 14.7 g. (0.176 mole) of methoxyamine hydrochloride was added to keep the solution orange in color. The reaction product mixture was poured over ice and the aqueous mixture filtered. The solid which was collected was allowed to dry. It was recrystallized from petroleum ether (b.p. 60°-71° C.) to yield material weighing 7.0 g. and having a melting point of about 90° C. The product was identified by NMR spectrum and elemental analyses as 2,6-dinitro-4-ethyl-N-methoxyaniline.

Analyses: Calcd. for $C_9H_{11}N_3O_5$:

|   | Theoretical | Found |
|---|---|---|
| C | 44.80% | 45.11% |
| H | 4.60 | 4.53 |
| N | 17.42 | 17.34 |

Following the same general procedure of Preparation 2 and using 21.6 g. (0.1 mole) of 2,6-dinitro-4-methylchlorobenzene, 12.5 g. (0.15 mole) of methoxyamine hydrochloride, and 25.25 g. (0.25 mole) of triethylamine, the following additional compound was prepared:

3. 2,6-Dinitro-N-methoxy-p-toluidine, having a melting point of about 141°-143° C., and identified by NMR spectrum and elemental analyses. Yield = 12.5 g.

Analyses: Calcd. for $C_8H_9N_3O_5$:

|   | Theoretical | Found |
|---|---|---|
| C | 42.30% | 42.50% |
| H | 3.99 | 3.87 |
| N | 18.50 | 18.42 |

PREPARATION 4

2,6-Dinitro-N-ethoxy-α,α,α-trifluoro-p-toluidine

A solution of 10.0 g. (0.037 mole) of 4-chloro-3,5-dinitrobenzotrifluoride in 100 ml. of ethanol was prepared, to which there was added 11.21 g. (0.111 mole) of triethylamine, followed, in about 30 seconds, by the addition of 4.46 g. (0.046 mole) of ethoxyamine hydrochloride. The reaction mixture was allowed to stir at ambient room temperature for about 1 hour and 15 minutes, at the end of which time, additional ethoxyamine hydrochloride, 4.46 g. (0.046 mole), was added, bringing about a color change of the reaction mixture and the evolution of heat. The reaction product mixture was then worked up by diluting it with water, making the solution acidic, and extracting the solution with several portions of ether. The combined ether extracts were washed several times with dilute acid and water and dried over anhydrous magnesium sulfate. The drying agent was filtered off and the filtrate was concentrated in vacuo to leave a residue. The residue was recrystallized from petroleum ether (b.p. 60°-71° C.) to yield a product having a melting point of about 96°-98° C., and weighing 9.0 g. The product was identified by NMR spectrum and elemental analyses as 2,6-dinitro-N-ethoxy-α,α,α-trifluoro-p-toluidine.

Analyses: Calcd. for $C_9H_8F_3N_3O_5$:

|   | Theoretical | Found |
|---|---|---|
| C | 36.62% | 36.66% |
| H | 2.73 | 2.47 |
| N | 14.24 | 14.09 |

PREPARATION 5

2,6-Dinitro-N-methoxy-α,α,α-trifluoro-p-toluidine

To a solution prepared from 27.0 g. (0.1 mole) of 4-chloro-3,5-dinitrobenzotrifluoride in 200 ml. of ethanol there was added 25.25 g. (0.25 mole) of triethylamine, and 12.5 g. (0.15 mole) of methoxyamine hydrochloride. Upon the addition of the methoxyamine hydrochloride, the temperature of the reaction mixture rose to about 50° C. The reaction mixture was allowed to stir for about 1.5 hours and the reaction product mixture was worked up by diluting it with ethyl acetate, washing several times with dilute hydrochloric acid and water, and drying the organic layer over anhydrous magnesium sulfate. The drying agent was filtered off and the filtrate concentrated on the steam bath to leave a residue. The residue was allowed to chill over the weekend in the refrigerator and crystals separated. The crystalline product was filtered off. It had a melting point of about 135°–137° C., weighed 21.0 g., and was identified by NMR spectrum and elemental analyses as 2,6-dinitro-N-methoxy-α,α,α-trifluoro-p-toluidine.

Analyses: Calcd. for $C_8H_6F_3N_3O_5$:

|   | Theoretical | Found |
|---|---|---|
| C | 34.18% | 34.17% |
| H | 2.15 | 2.12 |
| N | 14.95 | 14.82 |

Using the substituted N-alkoxy-2,6-dinitroanilines prepared as described above, the novel method of this invention is carried out and is illustrated by the following examples. As those skilled in the art will readily appreciate, other compounds can be made following this procedure, and therefore the scope of the invention is not to be considered as limited by this disclosure.

EXAMPLE 1

N-Allyl-2,6-dinitro-N-ethoxy-p-toluidine

A mixture of 2.5 g. (0.01 mole) of 2,6-dinitro-N-ethoxy-p-toluidine (see Preparation 1) and 0.015 mole of sodium hydride (prepared from 0.72 g. of a 50% dispersion of sodium hydride in mineral oil by repeated washings with hexane) in 75 ml. of dimethylformamide was prepared and allowed to stir for about 10 minutes at room temperature. At the end of that time, 2.42 g. (0.02 mole) of allyl bromide was added to the reaction mixture. The mixture was stirred for about 1 hour at room temperature. The reaction product mixture was worked up by adding ether and washing with dilute aqueous hydrochloric acid. The organic solution was dried over anhydrous magnesium sulfate, filtered, and the filtrate concentrated in vacuo to remove the solvent. The residue thus obtained was dissolved in toluene and chromatographed over a Florisil column, using toluene as the eluent. The solution collected from the column was concentrated and there was obtained 1.25 g. of an oil which was identified by its NMR spectrum and elemental analyses as N-allyl-2,6-dinitro-N-ethoxy-p-toluidine.

Analyses: Calcd. for $C_{12}H_{15}N_3O_5$:

|   | Theoretical | Found |
|---|---|---|
| C | 51.24% | 51.37% |
| H | 5.38 | 5.10 |
| N | 14.94 | 14.70 |

Following the same general procedure of Example 1, and using appropriate starting materials, as indicated, the following additional compounds were prepared and identified by NMR spectra and elemental analyses:

EXAMPLE 2

2,6-Dinitro-N-ethoxy-N-propyl-p-toluidine, as an oil weighing 1.2 g., from 5.0 g. (0.021 mole) of 2,6-dinitro-N-ethoxy-p-toluidine (Preparation 1), 3.39 g. (0.0203 mole) of n-propyl iodide, and 0.012 mole of sodium hydride, prepared from 0.59 g. of a 50% dispersion of sodium hydride in mineral oil.

Analyses: Calcd. for $C_{12}H_{17}N_3O_5$:

|   | Theoretical | Found |
|---|---|---|
| C | 50.88% | 50.60% |
| H | 6.05 | 5.80 |
| N | 14.83 | 14.57 |

EXAMPLE 3

N,4-Diethyl-2,6-dinitro-N-methoxyaniline, weighing 1.0 g., and having a melting point of about 80°–82° C., from 5.0 g. (0.021 mole) of 2,6-dinitro-4-ethyl-N-methoxyaniline (Preparation 2), 0.02 mole of sodium hydride obtained from 0.96 g. of a 50% dispersion of sodium hydride in mineral oil, and 6.24 g. (0.04 mole) of ethyl iodide.

Analyses: Calcd. for $C_{11}H_{15}N_3O_5$:

|   | Theoretical | Found |
|---|---|---|
| C | 49.07% | 49.19% |
| H | 5.62 | 5.37 |
| N | 15.61 | 15.42 |

EXAMPLE 4

2,6-Dinitro-4-ethyl-N-methoxy-N-propylaniline, having a melting point of about 72°–74° C., and weighing 1.5 g., from 3.0 g. (0.0124 mole) of 2,6-dinitro-4-ethyl-N-methoxyaniline (Preparation 2), 4.0 g. (0.024 mole) of n-propyl iodide, and 0.012 mole of sodium hydride obtained from 0.58 g. of a 50% dispersion of sodium hydride in mineral oil.

Analyses: Calcd. for $C_{12}H_{17}N_3O_5$:

|   | Theoretical | Found |
|---|---|---|
| C | 50.88% | 51.01% |
| H | 6.05 | 5.80 |
| N | 14.83 | 14.82 |

EXAMPLE 5

2,6-Dinitro-N-ethyl-N-methoxy-α,α,α-trifluoro-p-toluidine

To 0.017 mole of sodium hydride, obtained from 0.82 g. of a 50% dispersion of sodium hydride in mineral oil, was added 50 ml. of dimethylformamide. To the suspension, there was added 15.0 g. (0.017 mole) of 2,6-dinitro-N-methoxy-α,α,α-trifluoro-p-toluidine (Preparation 5), and the mixture was heated for about 45 minutes at temperatures up to about 65° C. The reaction mixtures was then cooled to room temperature and there was added thereto, dropwise, 5.3 g. (0.034 mole) of ethyl iodide. The mixture was allowed to stir at room temperature for about 30 minutes and then heated for about 1 hour at about 80° C., and was checked by TLC. No starting material appeared on the thin layer chromatogram. The reaction product mixture was cooled and allowed to stand overnight at ambient room temperature. The reaction product mixture was worked up by diluting it with ether and washing several times with dilute aqueous hydrochloric acid, once with water, and drying the organic phase over anhydrous magnesium sulfate. The drying agent was filtered off and the solvent removed in vacuo. The residue was chromatographed on a Florisil column using benzene both as solvent and as eluant. The first fractions collected appeared to contain the desired product. The fractions were combined, the solvent was removed in vacuo, and the residue thus obtained was recrystallized from petroleum ether (b.p. 60°–71° C.). The product had a melting point of about 95°–97° C., weighed 1.0 g., and was identified by NMR spectrum and elemental analyses as 2,6-dinitro-N-ethyl-N-methoxy-$\alpha,\alpha,\alpha$-trifluoro-p-toluidine.

Analyses: Calcd. for $C_{10}H_{10}F_3N_3O_5$:

|   | Theoretical | Found |
|---|---|---|
| C | 38.85% | 39.86% |
| H | 3.26 | 3.23 |
| N | 13.59 | 13.88 |

EXAMPLE 6

2,6-Dinitro-N-methoxy-N-propyl-$\alpha,\alpha,\alpha$-trifluoro-p-toluidine

Petroleum ether (b.p. 60°–71° C.) was stirred with 0.82 g. of a 50% dispersion of sodium hydride in mineral oil, and the petroleum ether solution of the mineral oil was removed by decanting. The 0.017 mole of sodium hydride remaining was suspended in 75 ml. of dimethylformamide and 5.0 g. (0.018 mole) of 2,6-dinitro-N-methoxy-$\alpha,\alpha,\alpha$-trifluoro-p-toluidine (Preparation 5) was added. The reaction mixture was heated for about 30 minutes to a temperature of about 65° C. The reaction mixture was then cooled to about room temperature and 5.78 g. (0.034 mole) of n-propyl iodide was added. The reaction mixture was heated to about 40° C. for a period of about 30 minutes, and the temperature was then gradually increased to about 100°–110° C. The heating time totaled about 2 hours. At the end of that time, the reaction product mixture was cooled and worked up by diluting it with ether and washing the mixture successively with dilute aqueous hydrochloric acid and water. The organic phase was dried over anhydrous magnesium sulfate. The drying agent was filtered off and the filtrate concentrated in vacuo to leave a residue. The residue was chromatographed on a Florisil column using benzene as solvent and eluant. The fractions from the column were concentrated to have a residue and the residue was recrystallized from petroleum ether (b.p. 60°–71° C.) The product obtained weighed 1.9 g., and had a melting point of about 59°–60° C. The product was identified by NMR spectrum and elemental analyses as 2,6-dinitro-N-methoxy-N-propyl-$\alpha,\alpha,\alpha$-trifluoro-p-toluidine.

Analyses: Calcd. for $C_{11}H_{12}F_3N_3O_5$:

|   | Theoretical | Found |
|---|---|---|
| C | 40.88% | 40.68% |
| H | 3.74 | 3.84 |
| N | 13.00 | 13.20 |

EXAMPLE 7

2,6-Dinitro-N-methallyl-N-methoxy-$\alpha,\alpha,\alpha$-trifluoro-p-toluidine

To 0.017 mole of sodium hydride, obtained from 0.82 g. of a 50% dispersion of sodium hydride in mineral oil (by the process described in Example 6, supra), was added 50 ml. of dimethylformamide. There was then added to the mixture of sodium hydride and dimethylformamide, 5.0 g. (0.018 mole) of 2,6-dinitro-N-methoxy-$\alpha,\alpha,\alpha$-trifluoro-p-toluidine (Preparation 5), and the reaction mixture heated to about 60° C. for about 20 minutes. The reaction mixture was then cooled to approximately room temperature and there was added 6.14 g. (0.068 mole) of methallyl chloride. The reaction mixture was heated to about 65° C. for about 30 minutes, following which the temperature of the reaction mixture was increased to about 90° C. and held there for about 2 hours, followed by heating for an additional 2 hours at about 110° C. The reaction product mixture was cooled, diluted with ether and washed with dilute aqueous hydrochloric acid and water. The ether layer was dried over anhydrous magnesium sulfate. The drying agent was filtered off and the filtrate concentrated in vacuo to remove the solvent. The residue was dissolved in benzene and chromatographed on a Florisil column, using benzene as the eluant. The first portion off the column was concentrated in vacuo to leave a residue which was recrystallized from petroleum ether (b.p. 60°–71° C.). There was obtained product weighing 0.5 g. and having a melting point of about 55°–56° C. The product was identified by NMR spectrum and elemental analyses as 2,6-dinitro-N-methallyl-N-methoxy-$\alpha,\alpha,\alpha$-trifluoro-p-toluidine.

Analyses: Calcd. for $C_{12}H_{12}F_3N_3O_5$:

|   | Theoretical | Found |
|---|---|---|
| C | 42.99% | 42.75% |
| H | 3.61 | 3.39 |
| N | 12.53 | 12.31 |

Following the same general procedure of Example 7, and using appropriate starting materials, as indicated, the following additional compound was prepared and identified by NMR spectrum and elemental analyses:

EXAMPLE 8

N-Allyl-2,6-dinitro-N-methoxy-$\alpha,\alpha,\alpha$-trifluoro-p-toluidine, weighing 2.4 g., and having a melting point of about 77°–79° C., from 5.0 g. (0.018 mole) of 2,6-dinitro-N-methoxy-$\alpha,\alpha,\alpha$-trifluoro-p-toluidine (Preparation 5), 4.11 g. (0.034 mole) of allyl bromide, and 0.42 g. (0.017 mole) of sodium hydride, obtained from 0.82 g. of a 50% dispersion of sodium hydride in mineral oil.

Analyses: Calcd. for $C_{11}H_{10}F_3N_3O_5$:

|   | Theoretical | Found |
|---|---|---|
| C | 41.13% | 41.15% |
| H | 3.14 | 3.09 |

-continued

Analyses: Calcd. for $C_{11}H_{10}F_3N_3O_5$:

|   | Theoretical | Found |
|---|---|---|
| N | 13.08 | 12.83 |

EXAMPLE 9

2,6-Dinitro-N-ethoxy-N-ethyl-α,α,α-trifluoro-p-toluidine

To 0.017 mole of sodium hydride, obtained from 0.82 g. of 50% dispersion of sodium hydride in mineral oil (by the process described in Example 6 supra), was added 50 ml. of dimethylformamide and 5.0 g. (0.017 mole) of 2,6-dinitro-N-ethoxy-α,α,α-trifluoro-p-toluidine (Preparation 4), and the mixture was stirred for about 20 minutes at room temperature. There was then added 5.3 g. (0.034 mole) of ethyl iodide and the reaction mixture was heated to about 85° C. for about 2.5 hours. The progress of the reaction was checked by NMR spectrum, which showed the presence of about 66 percent product and 33 percent starting material. Another 5.3 g. (0.034 mole) of ethyl iodide was added and the mixture was heated a little longer. The reaction product mixture was then allowed to cool and was diluted with ether. The ether mixture was washed several times with dilute aqueous hydrochloric acid, once with water, and dried over anhydrous magnesium sulfate. The drying agent was filtered off and the filtrate concentrated in vacuo to remove the solvent, leaving a residue. The residue was dissolved in benzene and chromatographed on a Florisil column using benzene as the eluant. The fractions which were collected were checked by NMR. The pure fractions were combined and the solvent evaporated to dryness. The product thus obtained weighed 0.65 g. and had a melting point of about 72°-75° C. The product was identified by NMR spectrum and elemental analyses as 2,6-dinitro-N-ethoxy-N-ethyl-α,α,α-trifluoro-p-toluidine.

Analyses: Calcd. for $C_{11}H_{12}F_3N_3O_5$:

|   | Theoretical | Found |
|---|---|---|
| C | 40.88% | 41.09% |
| H | 3.74 | 3.44 |
| N | 13.00 | 12.88 |

Following the same general procedure of Example 9, and using appropriate starting materials, as indicated, the following additional compounds were prepared and identified by NMR spectra and elemental analyses:

EXAMPLE 10

N-Allyl-2,6-dinitro-N-ethoxy-α,α,α-trifluoro-p-toluidine, weighing 1.15 g., and having a melting point of about 52°-54° C., from 5.0 g. (0.017 mole) of 2,6-dinitro-N-ethoxy-α,α,α-trifluoro-p-toluidine (Preparation 4), 4.11 g. (0.034 mole) of allyl bromide, and 0.017 mole of sodium hydride, obtained from 0.82 g. of a 50% dispersion of sodium hydride in mineral oil in the manner previously described.

Analyses: Calcd. for $C_{12}H_{12}F_3N_3O_5$:

|   | Theoretical | Found |
|---|---|---|
| C | 42.99% | 42.77% |
| H | 3.61 | 3.72 |
| N | 12.53 | 12.80 |

EXAMPLE 11

2,6-Dinitro-N-ethoxy-N-propyl-α,α, α-trifluoro-p-toluidine, weighing 1.0 g., and having a melting point of about 34°-35° C., from 5.0 g. (0.017 mole) of 2,6-dinitro-N-ethoxy-α,α,α-trifluoro-p-toluidine (Preparation 4), 5.78 g. (0.034 mole) of n-propyl iodide, and 0.017 mole of sodium hydride, obtained in the usual manner from 0.82 g. of a 50% dispersion of sodium hydride in mineral oil.

Analyses: Calcd. for $C_{12}H_{14}F_3N_3O_5$:

|   | Theoretical | Found |
|---|---|---|
| C | 42.74% | 42.99% |
| H | 4.18 | 4.36 |
| N | 12.46 | 12.59 |

EXAMPLE 12

2,6-Dinitro-N-ethyl-N-methoxy-p-toluidine

To 0.017 mole of sodium hydride, obtained from 0.82 g. of a 50% dispersion of sodium hydride in mineral oil (by the process described in Example 6, supra), was added 50 ml. of dimethylformamide, followed by 4.54 g. (0.02 mole) of 2,6-dinitro-N-methoxy-p-toluidine (Preparation 3), with continuous mechanical stirring. The temperature of the mixture rose to about 40° C. Stirring was continued for about 10 minutes, followed by addition of 12.48 g. (0.08 mole) of ethyl iodide. The temperature of the reaction mixture was increased to about 90° C., and stirring continued for about 30 minutes. The progress of the reaction was checked by running an NMR spectrum on a small sample of the reaction mixture. The NMR spectrum showed mostly product was present. The reaction product mixture was stirred and heated at about 90° C. for another 30 minutes. The reaction product mixture was allowed to cool and was diluted with ether. It was washed with dilute aqueous hydrochloric acid and then with water. The organic layer was dried over anhydrous magnesium sulfate, the drying agent filtered off, and the solvent removed in vacuo. The residue was recrystallized from a mixture of petroleum ether (b.p. 60°-71° C.)-ethyl acetate, to yield product having a melting point of about 47°-50° C., and weighing 1.7 g. The product was identified by NMR spectrum and elemental analyses as 2,6-dinitro-N-ethyl-N-methoxy-p-toluidine.

Analyses: Calcd. for $C_{10}H_{13}N_3O_5$:

|   | Theoretical | Found |
|---|---|---|
| C | 47.06% | 47.06% |
| H | 5.13 | 5.02 |
| N | 16.46 | 16.46 |

Following the same general procedure of Example 12, and using appropriate starting materials, as indicated, the following additional compounds were prepared and identified by NMR spectra and elemental analyses:

EXAMPLE 13

2,6-Dinitro-N-methoxy-N-propyl-p-toluidine, as an oil, weighing 0.8 g., from 2.0 g. (0.009 mole) of 2,6-dinitro-N-methoxy-p-toluidine (Preparation 3), 3.4 g. (0.02 mole) of n-propyl iodide, and 0.5 g. (0.01 mole) a 50% dispersion of sodium hydride in mineral oil.

Analyses: Calcd. for $C_{11}H_{15}N_3O_5$:

|   | Theoretical | Found |
|---|---|---|
| C | 49.07% | 49.30% |
| H | 5.62 | 5.36 |
| N | 15.61 | 15.62 |

EXAMPLE 14

N-Allyl-2,6-dinitro-N-methoxy-p-toluidine, having a melting point of about 80°–82° C., and weighing 0.67 g., from 4.5 g. (0.02 mole) of 2,6-dinitro-N-methoxy-p-toluidine (Preparation 3), 4.8 g. (0.04 mole) of allyl bromide, and 0.96 g. (0.02 mole) of a 50% dispersion of sodium hydride in mineral oil.

Analyses: Calcd. for $C_{11}H_{13}N_3O_5$:

|   | Theoretical | Found |
|---|---|---|
| C | 49.44% | 49.29 |
| H | 4.90 | 4.78 |
| N | 15.72 | 15.59 |

EXAMPLE 15

N-Allyl-2,6-dinitro-4-ethyl-N-methoxyaniline

To 0.017 mole of sodium hydride, obtained from 0.82 g. of a 50% dispersion of sodium hydride in mineral oil (by the process described in Example 6, supra), was added 50 ml. of dimethylformamide. To the suspension was added 3.0 g. (0.012 mole) of 2,6-dinitro-4-ethyl-N-methoxyaniline (Preparation 2), and the mixture stirred for about 5–10 minutes. Allyl bromide, 2.9 g. (0.024 mole), was added and the reaction mixture stirred at room temperature for about 30 minutes. A sample of the reaction mixture checked by NMR showed the presence of about 70–80 percent of the desired product, together with about 20–30 percent of starting material. The reaction mixture was then heated at about 90° C., with stirring, for about an hour. A check by NMR indicated the reaction had gone to completion. The reaction product mixture was worked up by adding dilute aqueous hydrochloric acid and toluene. The organic layer was separated and dried over anhydrous magnesium sulfate. The drying agent was filtered off and the filtrate was chromatographed on a Florisil column. The fractions were examined by NMR spectrum, combined, and concentrated in vacuo to dryness. The residue was recrystallized from petroleum ether (b.p. 60°–71° C.) to give 1.7 g. of product having a melting point of about 83°–85° C. The product was identified by NMR spectrum and elemental analyses as N-allyl-2,6-dinitro-4-ethyl-N-methoxyaniline.

Analyses: Calcd. for $C_{12}H_{15}N_3O_5$:

|   | Theoretical | Found |
|---|---|---|
| C | 51.24% | 51.46% |
| H | 5.38 | 5.32 |
| N | 14.94 | 14.69 |

EXAMPLE 16

2,6-Dinitro-4-ethyl-N-methoxy-N-methylaniline

A suspension of 5.8 g. of (0.024 mole) of 2,6-dinitro-4-ethyl-N-methoxyaniline (Preparation 2), and 1.15 g. (0.024 mole) of a 50% dispersion of sodium hydride in mineral oil was prepared in 50 ml. of dimethylformamide. The mixture was stirred for about 10 minutes at room temperature, during which time the reaction temperature rose to about 50° C. There was then added 6.76 g. (0.048 mole) of methyl iodide, with continued stirring for about 30 minutes, during which time the temperature of the reaction mixture rose to about 90° C., with no external heating. The reaction mixture was checked by TLC, which showed the absence of starting material. The reaction product mixture was allowed to cool. The mixture was diluted with dilute aqueous hydrochloric acid and toluene, the organic layer separated, and dried over anhydrous magnesium sulfate. The drying agent was filtered off and the filtrate was chromatographed on a Florisil column, using toluene as the eluant. Two products came off the column at the same time. The mixture of two compounds was dissolved in a 75 percent benzene:25 percent petroleum ether (b.p. 60°–71° C.) mixture, and again chromatographed on a Florisil column. Fractions were collected from the column and checked by their NMR spectra. The desired product was the second to come off the column. The fractions containing the desired product were combined, concentrated in vacuo, and the residue thus obtained was recrystallized from petroleum ether (b.p. 60°–71° C.) to yield product weighing 0.7 g., and having a melting point of about 85°–87° C. The product was identified by NMR spectrum and elemental analyses as 2,6-dinitro-4-ethyl-N-methoxy-N-methylaniline.

Analyses: Calcd. for $C_{10}H_{13}N_3O_5$:

|   | Theoretical | Found |
|---|---|---|
| C | 47.06% | 47.05% |
| H | 5.13 | 4.98 |
| N | 16.46 | 16.70 |

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the apended claims.

I claim:

1. A method of preparing substituted N-alkoxy-N-substituted-2,6-dinitroanilines of the formula

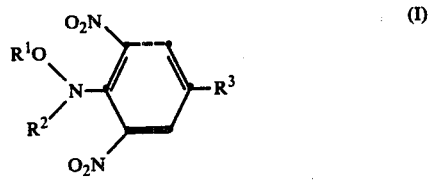

(I)

wherein
$R^1$ is methyl or ethyl;
$R^2$ is $C_1$–$C_3$ alkyl or $C_3$–$C_4$ alkenyl; and
$R^3$ is methyl, ethyl, or trifluoromethyl, which comprises allowing a compound of the formula:

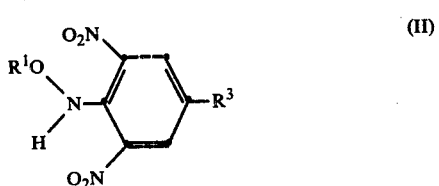

(II)

to react with an alkylating agent selected from the group consisting of a $C_1$–$C_3$ alkyl halide and a $C_3$–$C_4$ alkenyl halide, in dimethylformamide in the presence of sodium hydride.

2. The method of claim 1 wherein the alkylating agent is allyl bromide, $R^1$ is ethyl, and $R^3$ is methyl.

3. The method of claim 1 wherein the alkylating agent is ethyl iodide, $R^1$ is methyl, and $R^3$ is trifluoromethyl.

4. The method of claim 1 wherein the alkylating agent is n-propyl iodide, $R^1$ is methyl, and $R^3$ is trifluoromethyl.

5. The method of claim 1 wherein the alkylating agent is methallyl chloride, $R^1$ is methyl, and $R^3$ is trifluoromethyl.

* * * * *